United States Patent
Duffy et al.

(10) Patent No.: US 9,271,856 B2
(45) Date of Patent: Mar. 1, 2016

(54) DELIVERY CATHETER WITH DISTAL MOVING CAPSULE FOR TRANSAPICAL PROSTHETIC HEART VALVE DELIVERY

(75) Inventors: Niall Duffy, Ballygluinin (IE); Ronan Rogers, Galway (IE); John Gallagher, Dublin (IE); Gavin Kenny, Ballybrit (IE)

(73) Assignee: Medtronic Vascular Galway, Ballybrit, Galway (IE)

( * ) Notice: Subject to any disclaimer, the term of this patent is extended or adjusted under 35 U.S.C. 154(b) by 690 days.

(21) Appl. No.: 13/557,488

(22) Filed: Jul. 25, 2012

(65) Prior Publication Data

US 2014/0031922 A1  Jan. 30, 2014

(51) Int. Cl.
*A61F 2/24* (2006.01)
*A61F 2/966* (2013.01)
*A61F 2/95* (2013.01)

(52) U.S. Cl.
CPC .............. *A61F 2/966* (2013.01); *A61F 2/2436* (2013.01); *A61F 2002/9505* (2013.01); *A61F 2002/9517* (2013.01); *A61F 2002/9665* (2013.01)

(58) Field of Classification Search
CPC .................. A61F 2/966; A61F 2/2436; A61F 2002/9517; A61F 2002/9665; A61F 2002/9505
See application file for complete search history.

(56) References Cited

U.S. PATENT DOCUMENTS

| | | | |
|---|---|---|---|
| 5,824,041 A | 10/1998 | Lenker et al. | |
| 7,914,569 B2 | 3/2011 | Nguyen et al. | |
| 8,016,877 B2 | 9/2011 | Seguin et al. | |
| 2010/0286768 A1* | 11/2010 | Alkhatib | 623/2.11 |
| 2011/0251665 A1 | 10/2011 | Schmitt et al. | |
| 2011/0307049 A1 | 12/2011 | Kao | |
| 2012/0035717 A1 | 2/2012 | Duffy et al. | |

FOREIGN PATENT DOCUMENTS

| | | |
|---|---|---|
| WO | WO2007/035471 | 3/2007 |
| WO | WO2008/138584 | 11/2008 |
| WO | WO2009/091509 | 7/2009 |
| WO | WO2011/102968 | 8/2011 |

\* cited by examiner

*Primary Examiner* — Gregory Anderson
*Assistant Examiner* — Son Dang

(57) ABSTRACT

Heart valve delivery systems and methods of delivering and implanting heart valves using delivery catheters are disclosed. The delivery systems can include a handle assembly with a rotatable control knob and a catheter including an introducer shaft, an intermediate shaft extending from the handle assembly, an inner shaft extending from the handle assembly, and a capsule for containing a prosthesis. The distal end of the capsule can be connected to a distal end of the inner shaft, which can be moved in a distal direction by the rotatable control knob to deploy the prosthesis. By advancing the introducer through the deployed prosthesis and retracting the capsule to mate with the introducer, a smooth profile can be created for retraction of the system through the deployed prosthesis, minimizing hang-ups and snagging.

20 Claims, 16 Drawing Sheets

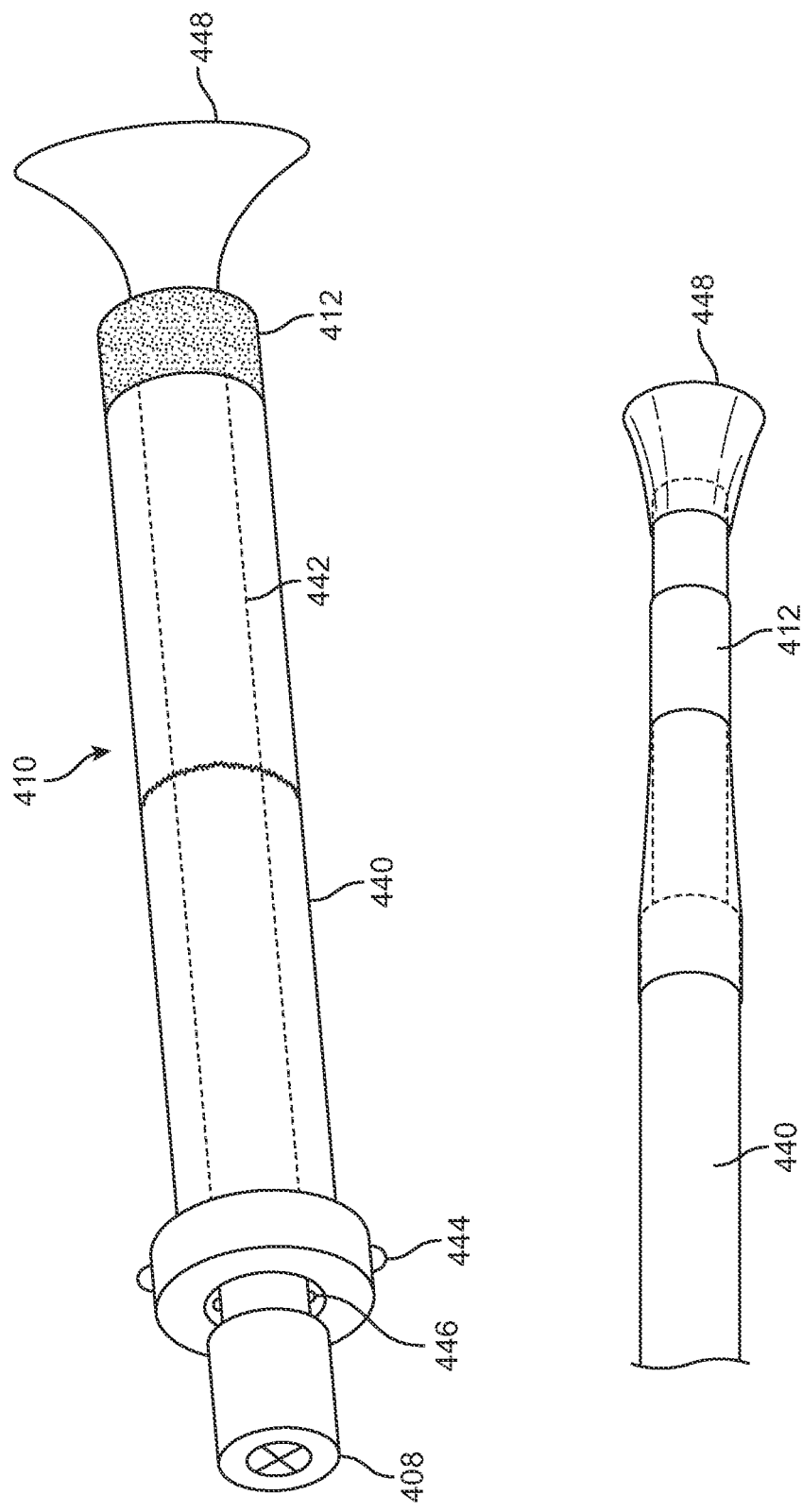

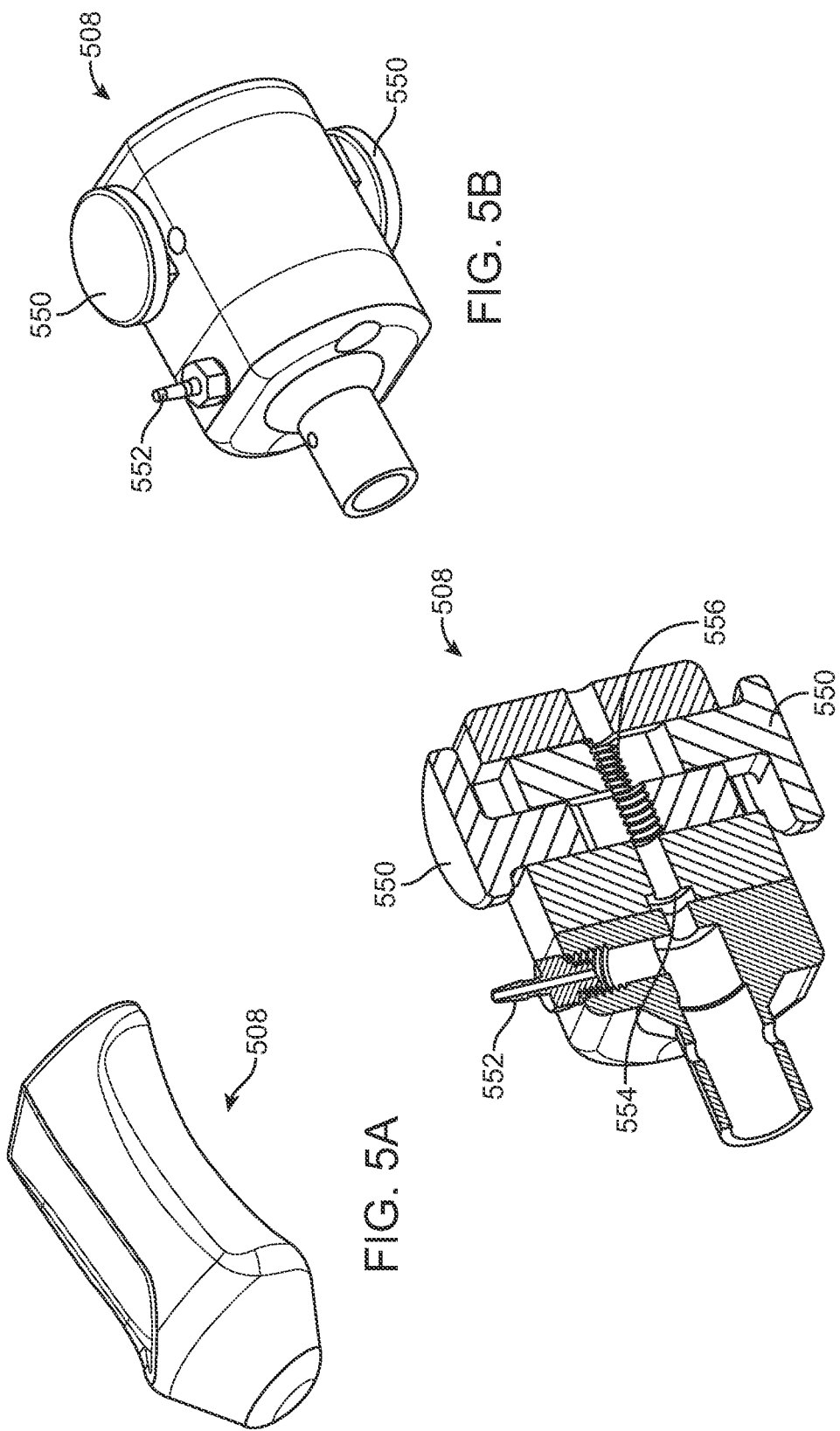

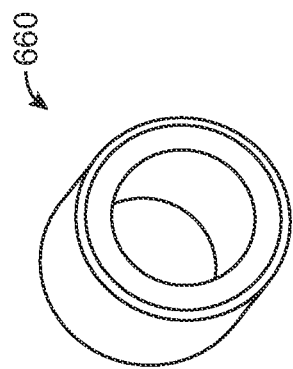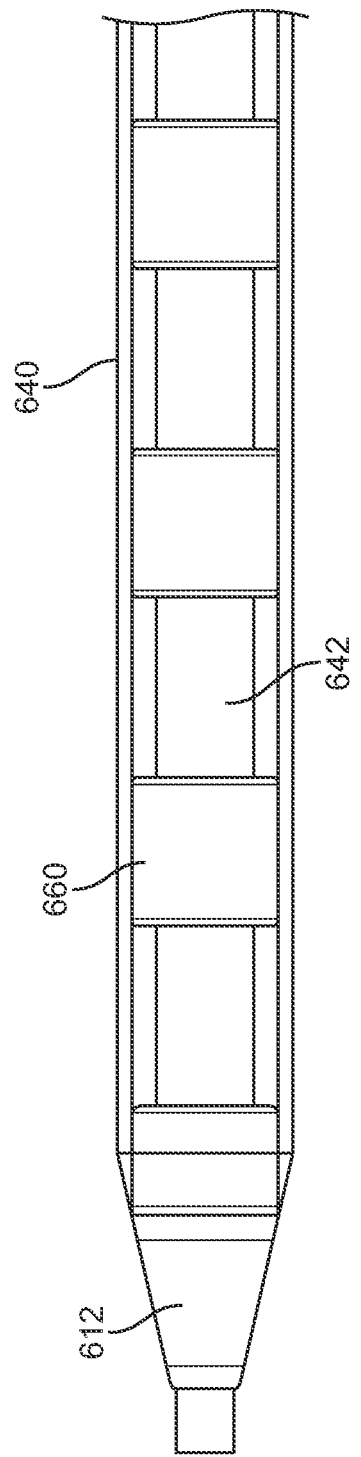
FIG. 6A
FIG. 6B

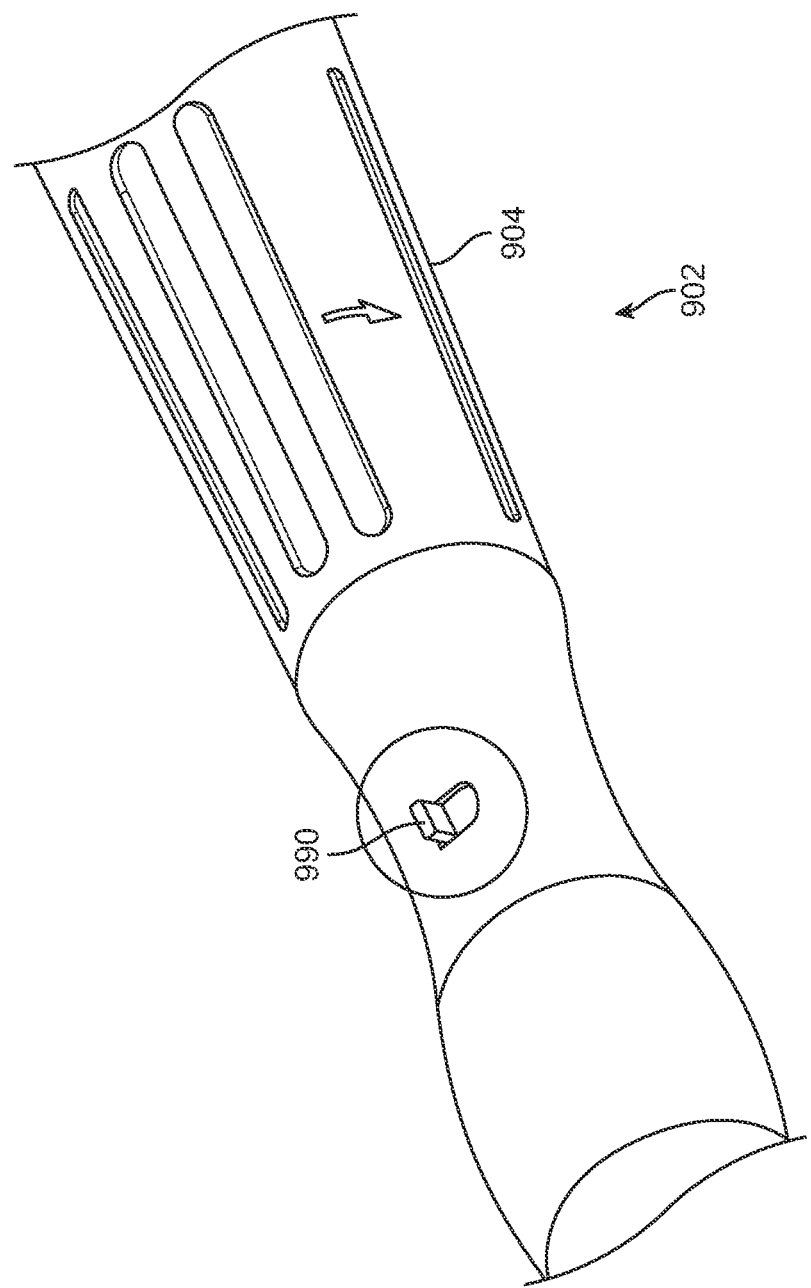

DELIVERY CATHETER WITH DISTAL MOVING CAPSULE FOR TRANSAPICAL PROSTHETIC HEART VALVE DELIVERY

BACKGROUND

1. Field

The present disclosure relates to heart valve delivery systems and methods of delivering and implanting heart valves using delivery catheters. More specifically, the present disclosure relates to delivery systems with a distal moving capsule for transapical delivery of a prosthetic heart valve.

2. Background

Recently, minimally invasive approaches have been developed to facilitate catheter-based implantation of valve prostheses on the beating heart, intending to obviate the need for the use of classical sternotomy and cardiopulmonary bypass. For example, U.S. Pat. No. 8,016,877 to Seguin et al. illustrates a technique and a device for replacing a deficient heart valve by percutaneous route. An expandable prosthetic valve can be compressed about a catheter, inserted inside a lumen within the body, such as the femoral artery, and delivered to a desired location in the heart. Additionally, U.S. Pat. No. 7,914,569 to Nguyen et al. discloses advancing a catheter containing a prosthesis in a retrograde manner through the femoral artery and into the descending aorta, over the aortic arch, through the ascending aorta and inside the defective aortic valve. This procedure can be assisted by fluoroscopic guidance. Once the position of the catheter containing the prosthesis is confirmed, a sheath containing the prosthesis can be moved proximally, allowing the valve prosthesis to self-expand.

With regard to the structure of the heart valve prosthesis itself, U.S. Pat. No. 7,914,569 to Nguyen et al. describes an example prosthesis for percutaneous transluminal delivery, and is incorporated by reference herein in its entirety. The heart valve prosthesis can have a self-expanding multi-level frame that supports a valve body with a skirt and plurality of leaflets. The frame can be contracted during percutaneous transluminal delivery and expanded to an hourglass shape upon deployment within the native heart valve.

Other techniques for delivering prosthetic heart valves via a catheter include a transapical approach for aortic valve replacement, typically involving the use of an introducer port, i.e., a large-bore overtube, of a trocar. A crimped, framed valve prosthesis reversibly coupled to a delivery catheter can be transcatheterally advanced toward the native valve, where it can be either forcefully deployed using a balloon catheter, or, alternatively, passively deployed using a self-expandable system.

BRIEF SUMMARY

The present disclosure relates to delivery systems with a distal moving capsule to deploy a heart valve prosthesis. Inherent in this procedure is the potential for hang-ups upon deployment and catching or snagging on the deployed prosthesis during removal of the delivery system, which can impact the user's ability to perform the procedure safely. The present disclosure provides delivery systems which can minimize the procedural risks of hang-ups upon deployment and snagging during removal of the delivery system after implantation. The delivery systems described herein can remedy one or more of the disadvantages of previous heart valve delivery systems by providing delivery systems with a continuous profile along the length of the delivery system before and after delivery of the heart valve prosthesis. The delivery systems provided herein can also include components that limit trauma to the expanded prosthetic valve and body channels as the delivery system is withdrawn through the expanded valve and thereafter from the body.

The delivery systems disclosed can include a handle assembly with a rotatable control knob. The delivery systems can also include a catheter including an introducer shaft having an interior lumen and an introducer tip, an intermediate shaft extending from the handle assembly and having an interior lumen, an inner shaft extending from the handle assembly, and a capsule for containing a prosthesis. The introducer shaft can be connected to a hub, which can be secured to the intermediate shaft and configured to slide along the intermediate shaft. The distal end of the capsule can be connected to a distal end of the inner shaft, which can be moved in a proximal and distal direction by the rotatable control knob.

Methods of delivering a prosthetic device are also disclosed. The prosthetic device can be delivered by inserting the catheter into a body lumen, advancing the catheter to a deployment location, and advancing the capsule distally to deploy the prosthetic device. The catheter can then be closed and withdrawn from the body lumen by advancing the introducer shaft through the deployed prosthetic device until the introducer tip engages the proximal end of the capsule, retracting the catheter proximally through the deployed prosthetic device, and removing the catheter from the body lumen.

BRIEF DESCRIPTION OF THE DRAWINGS/FIGURES

The accompanying figures, which are incorporated herein, form part of the specification and illustrate embodiments of delivery systems and methods of delivering a prosthetic device to a desired location in a body of a patient. Together with the description, the figures further serve to explain the principles of and allow for the making and using of the delivery systems and methods described herein. These figures are intended to be illustrative, not limiting. Although the disclosure is generally described in the context of these embodiments, it should be understood that it is not intended to limit the scope of the disclosure to these particular embodiments. In the drawings, like reference numbers indicate identical or functionally similar elements.

FIGS. 4A and 4B illustrate an embodiment of the introducer including a flared distal tip.

FIGS. 5A-5C illustrate certain embodiments of the hub.

FIGS. 6A and 6B illustrate spacer beads that can be incorporated into the introducer, according to an embodiment.

FIGS. 9A-9C illustrate a handle safety stop feature, according to an embodiment.

DETAILED DESCRIPTION

Figure 1:
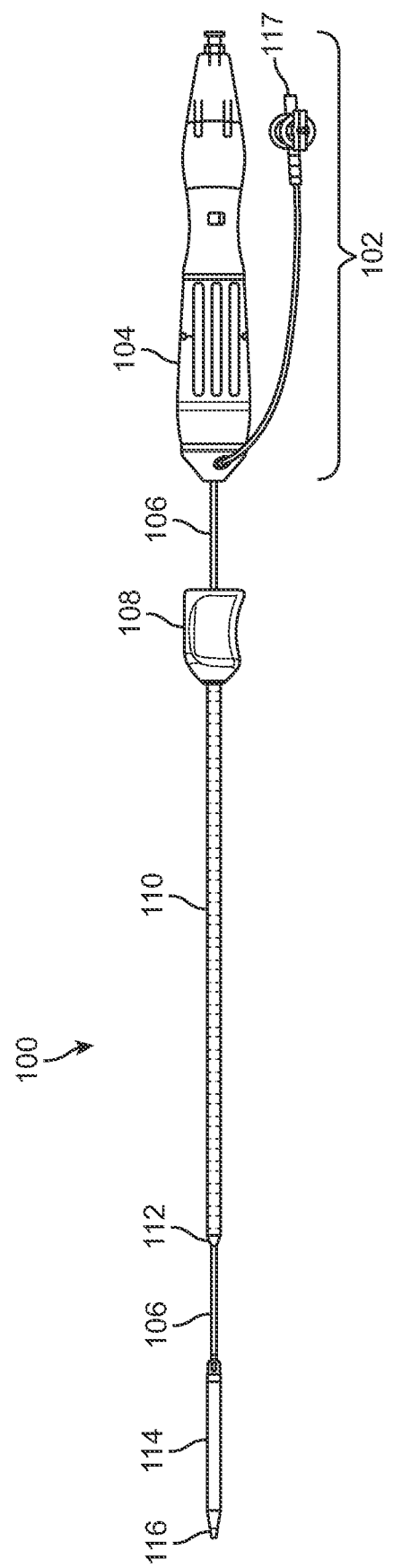
FIG. 1 illustrates the delivery system, according to an embodiment.

The following detailed description of heart valve delivery catheters and methods of delivering and implanting heart valves refers to the accompanying figures that illustrate example embodiments. Other embodiments are possible. Modifications can be made to the embodiments described herein without departing from the spirit and scope of the present disclosure. Therefore, the following detailed description is not meant to be limiting. Further, it would be apparent to one of skill in the art that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented. For example, while the description provided is directed to catheters for transapical delivery of a prosthetic heart valve, the catheters and individual features of the catheters described herein should not be limited to transapical delivery of a prosthetic heart valve. One of skill in the art would readily understand how to incorporate the features and structures described herein into catheters intended for other purposes. For example, features of the catheters described herein can be incorporated into catheters intended for other types of transluminal prosthetic heart valve delivery as well as catheters intended for thorascopic heart valve delivery. Features of the catheters described herein can also be incorporated into catheters designed for delivery of stents or valves to areas of the body other than the heart.

The present disclosure describes transapical delivery of transcatheter heart valve using a catheter with a capsule that travels distally. Inherent in this procedure is the potential for hang-ups upon deployment and catching or snagging on the deployed prosthesis during removal of the delivery system, which can impact the user's ability to perform the procedure safely.

The delivery systems disclosed can minimize the problems observed with other delivery systems such as snagging, hang-ups, flaring and "train wrecking" of the capsule. All of these can potentially cause damage to the prosthesis, injury to the patient or result in a major adverse clinical event.

The continuous profile of the disclosed delivery systems can provide smooth prosthesis deployment and delivery system retraction. The continuous profile can eliminate edges which can cause the system to hang-up or snag on the prosthesis during retraction.

The delivery systems disclosed can include a catheter designed for, but not limited to, use in a transapical procedure for the implantation of a prosthetic aortic valve. The systems can comprise a catheter with a distal moving capsule that can house a prosthetic valve. Movement of the capsule can be controlled by the user with a control knob in a handle at the proximal end of the catheter. The capsule can comprise a flexible tube or sheath with a rigid ring located at the proximal end. The capsule can be constructed of a single material or a multi-layer composite material such as an inner polymer layer made from a material with a low coefficient of friction (e.g., HDPE or PTFE) to assist in loading the prosthesis; a middle layer made of a metal laser cut tube, wound coil, braid, or similar structure to provide mechanical strength; and an outer layer made from a flexible polymer.

The catheter can comprise a sheath that can function as an integrated introducer and hemostasis control device. The introducer can be used as a dilator to widen the septum of the heart upon entry of the delivery system. It can also facilitate safe removal of the system from the body after deployment of the prosthesis. The catheter can include a number of design features to accomplish this, such as, but not limited to: a radiopaque atraumatic tip for tracking through the deployed prosthesis; a shaft that provides a balance of column strength, kink resistance and flexibility for tracking through the anatomy; and a hub that can include an integrated hemostasis control feature.

Prior to delivery, the capsule can be mated with the introducer tip to provide a smooth, edge-free surface for insertion of the delivery catheter through a procedure access point, and again for retraction of the system after deployment of the prosthesis. Mating of the capsule with the introducer tip after deployment of the prosthesis can be controlled with an integrated feature in the handle, so as to minimize the potential for user error that could possibly cause damage to the system or the patient.

The catheter can also include a component that acts as a retainer for the prosthesis prior to deployment. The retainer can have clips that allow the prosthesis to be releaseably attached to the retainer. The retainer can be made of a rigid material and can include a long section that acts as "landing zone" for the proximal end of the capsule upon deployment. The capsule can include a rigid ring that can mate with the landing zone of the valve retainer, and prevent the capsule from "fish mouthing" upon deployment, which could potentially lead to procedural complications.

FIG. 1 generally illustrates delivery system 100, according to an embodiment. Delivery system 100 can include handle 102, which can include control knob 104 and flushing port 117. Delivery system 100 can also include intermediate shaft 106, hub 108, introducer 110, introducer tip 112, capsule 114, and capsule tip 116. Components of delivery system 100 will be described in further detail below.

Figure 2A:
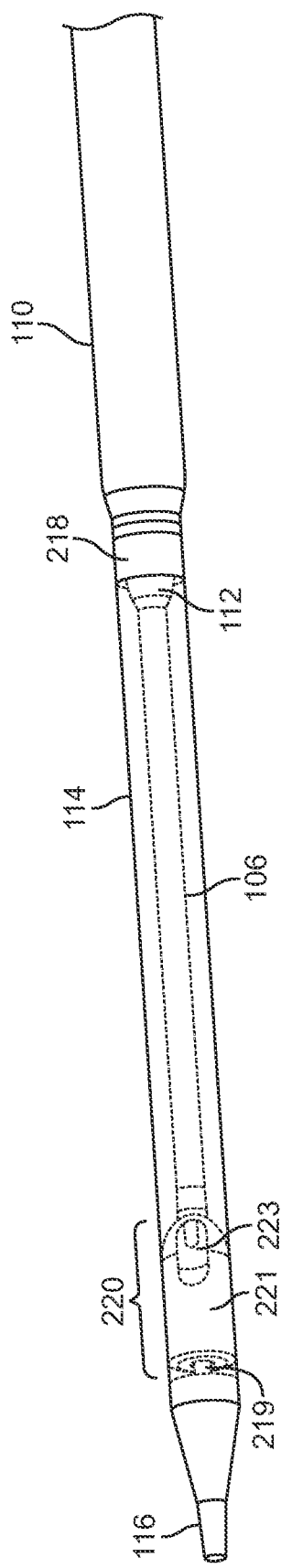
FIGS. 2A-2D illustrate the distal portion of the delivery system during the process of deployment and retraction, according to an embodiment.

FIGS. 2A-2D illustrate the distal portion of delivery system 100 during the deployment and retraction sequence, according to an embodiment. FIG. 2A illustrates the distal portion of delivery system 100 during the delivery stage. Introducer tip 112 can fit within the proximal portion of capsule 114. Capsule ring 218, located at the proximal end of capsule 114, can create a continuous profile between capsule 114 and introducer 110. Intermediate shaft 106 can be located within capsule 114, and during the procedure would have a prosthesis crimped about it. Valve retainer 220 can be located at the distal end of intermediate shaft 106. Valve retainer 220 can include landing zone 221 and one or more clip 223. Landing zone 221 can provide a surface for interfacing with capsule ring 218 after deployment of the prosthesis, when capsule 114 has been moved in the distal direction. One or more clips 223 can be used for holding the prosthesis in place during delivery. Clip 223 can comprise a traditional clip retention mechanism, a hook mechanism, or any other mechanism to facilitate retention of the prosthesis during delivery.

Figure 2B:
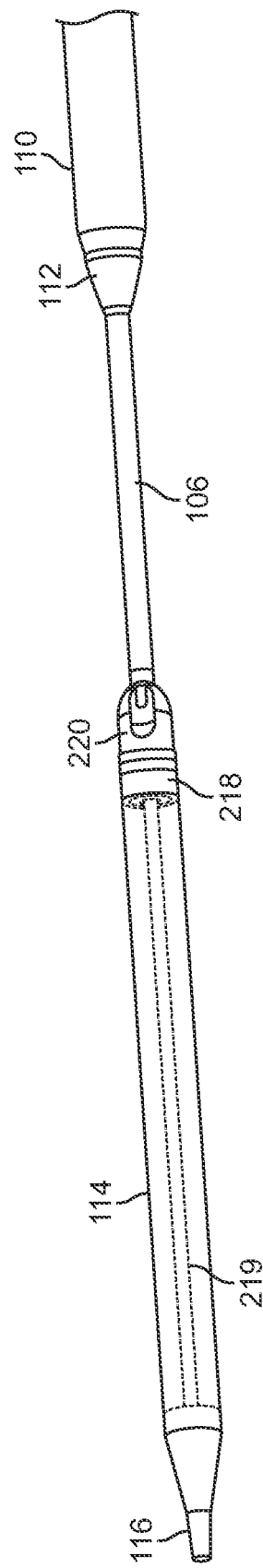

FIG. 2B illustrates the distal portion of delivery system 100 during the deployment stage. Once the delivery system, and in particular capsule tip 116, is advanced to the desired anatomical deployment position, capsule 114 can be advanced distally to deploy the prosthesis. Capsule 114 can be advanced by rotating control knob 104 on handle 102 such that inner shaft 219, which can be attached to capsule tip 116, moves in the distal direction. An interference fit can be created between capsule ring 218 and landing zone 221 of valve retainer 220. This can prevent capsule 114 from extending beyond valve retainer 220 during the deployment procedure.

Figure 2C:
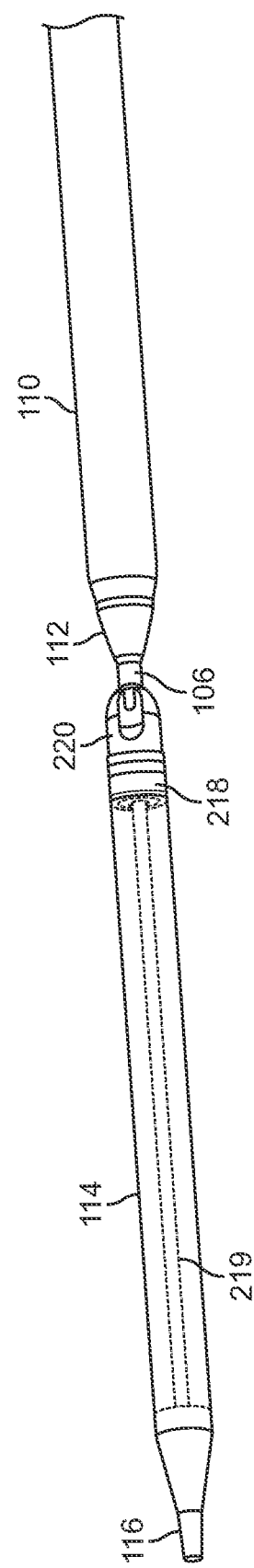

FIG. 2C illustrates the advancement stage of introducer 110, after deployment of the prosthesis. Introducer 110 can be advanced through the deployed prosthesis by pushing hub 108 (not shown) in the distal direction. Introducer 110 can be advanced until it contacts valve retainer 220. Introducer tip 112 can mate with valve retainer 220, maintaining a continuous profile of delivery system 100.

Figure 2D:
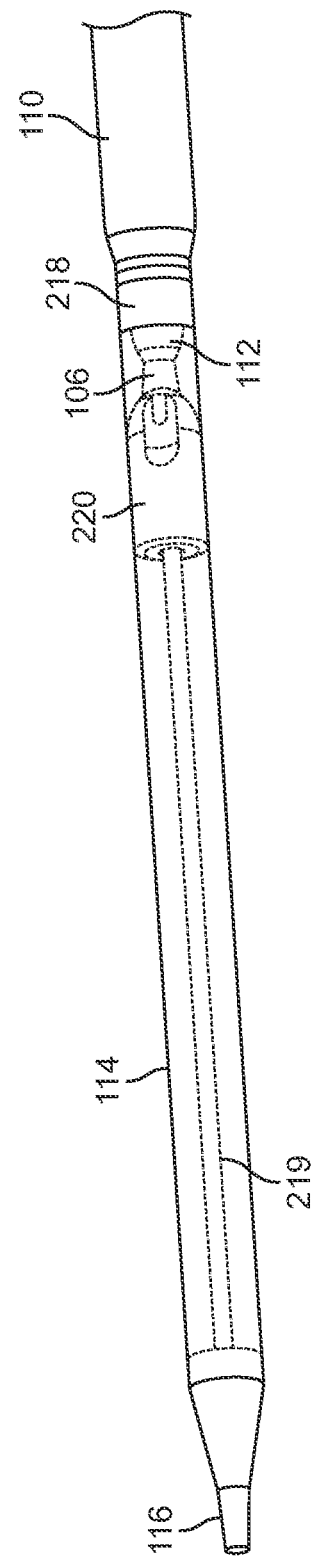

FIG. 2D illustrates the retraction stage, after deployment of the prosthesis and advancement of introducer 110 through the deployed prosthesis. Capsule 114 can be retracted proximally by rotating control knob 104 on handle 102 in a direction opposite to the direction that advances capsule 114. In certain embodiments, handle 102 can include a rapid retraction mechanism to retract capsule 114 in the distal direction. Capsule 114 can be retracted proximally until capsule ring 218 mates with introducer tip 112. Mating introducer tip 112 with capsule 114 can provide for easy withdrawal of delivery system 100 due to the stiffness of introducer 110 relative to capsule 114. This can also provide a smooth transition in the profile of delivery system 100 and can eliminate possible edges, thus minimizing the potential of delivery system 100 to snag or catch on the deployed prosthesis during retraction of delivery system 100 back through the deployed prosthesis.

Figure 3A:
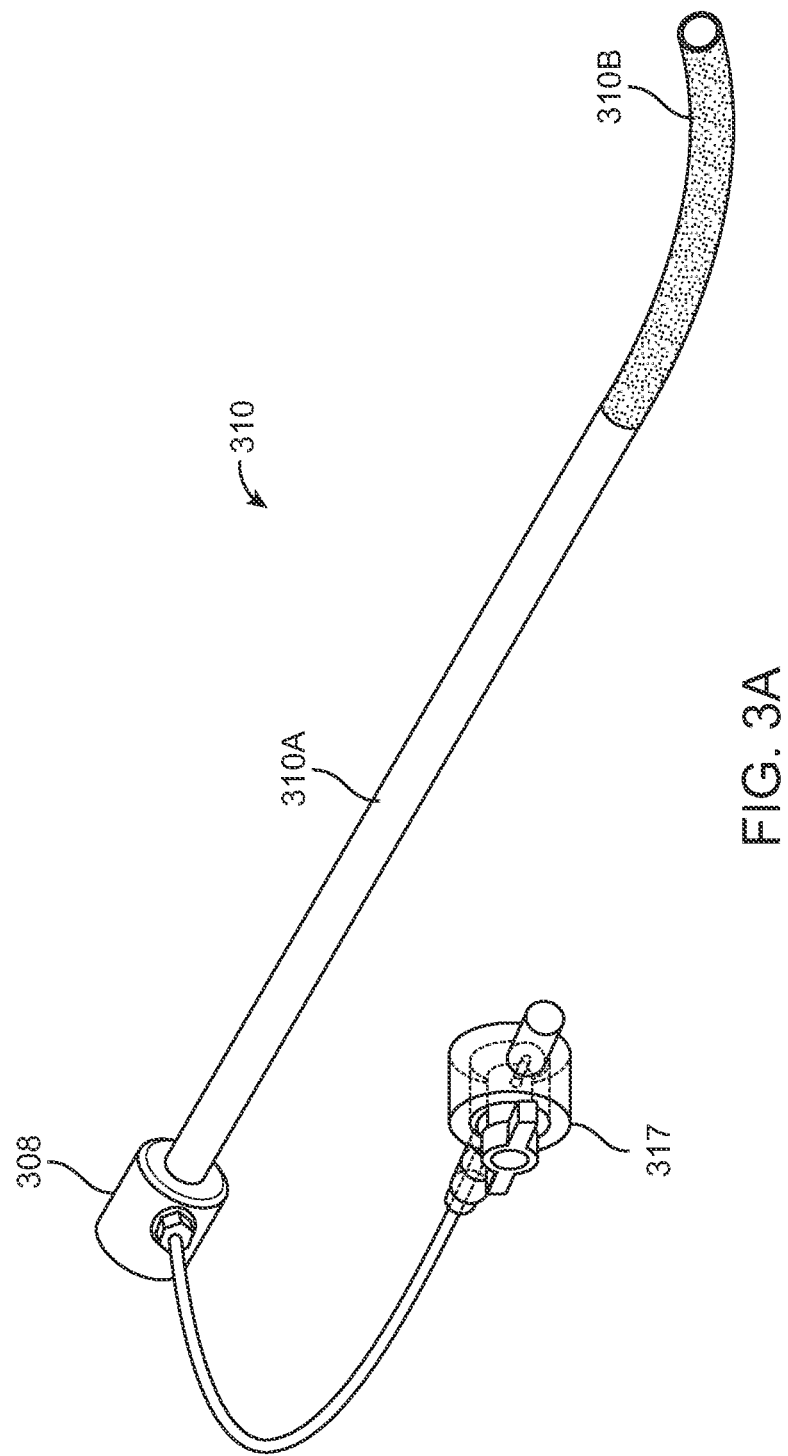
FIG. 3A illustrates an introducer, according to an embodiment.

FIGS. 3A-3D illustrate another embodiment of the delivery system. FIG. 3A illustrates an embodiment with a shaped introducer 310. Introducer 310 can include a stiff proximal section 310A and a flexible distal section 310B. Stiff proximal section 310A can provide the user with tactile feedback and provide a rigid structure to push flexible distal section 310B through the anatomy of the patient. Flexible distal section 310B can allow introducer 310 to track through the anatomy and be advanced up to capsule 314. Flexible distal section 310B can have a curved shape to facilitate movement through a curved body lumen. Introducer 310 can cover the exposed edges of capsule 314 and can provide for safe retraction through the deployed prosthesis. Introducer 310 can also include hub 308 and flushing port 317, which can perform similar functions as in other embodiments.

Figure 3B:
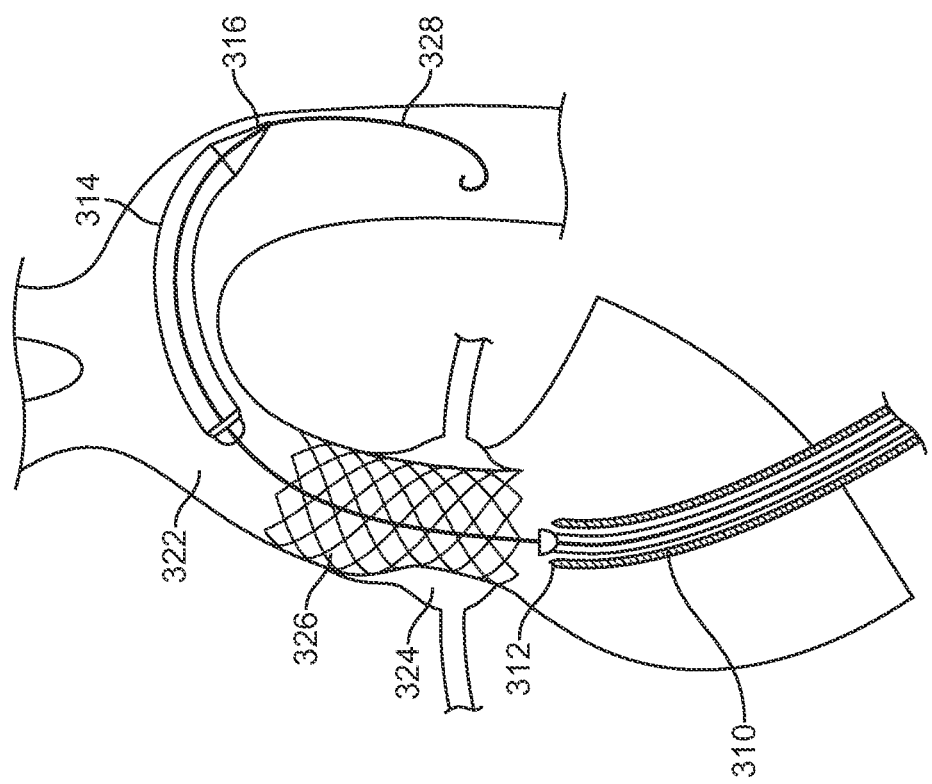
FIG. 3B illustrates the delivery system of FIG. 3A, according to an embodiment, after deploying a heart valve prosthesis.

FIG. 3B shows the delivery system of FIG. 3A after deployment of heart valve prosthesis 326. Capsule 314 has been advanced distally along guide wire 328 through aorta 322, allowing heart valve prosthesis 326 to be deployed within aortic sinus 324.

Figure 3D:
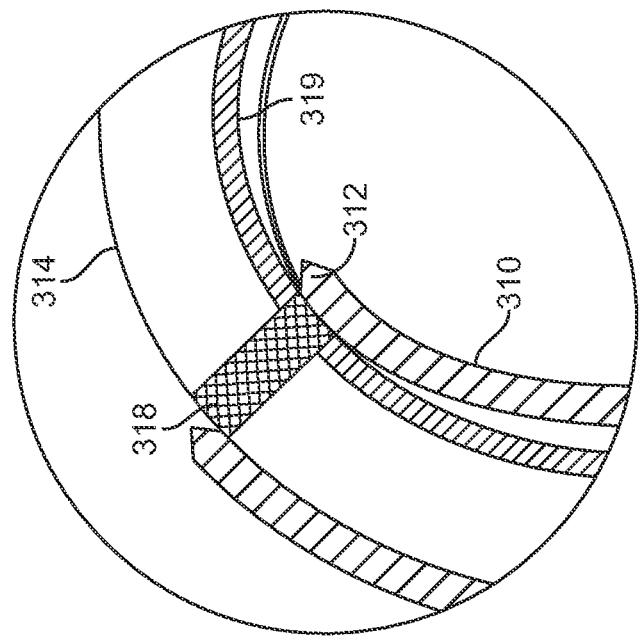
FIG. 3D illustrates an enlarged view of the introducer tip mating with the capsule, according to an embodiment.
Figure 3C:
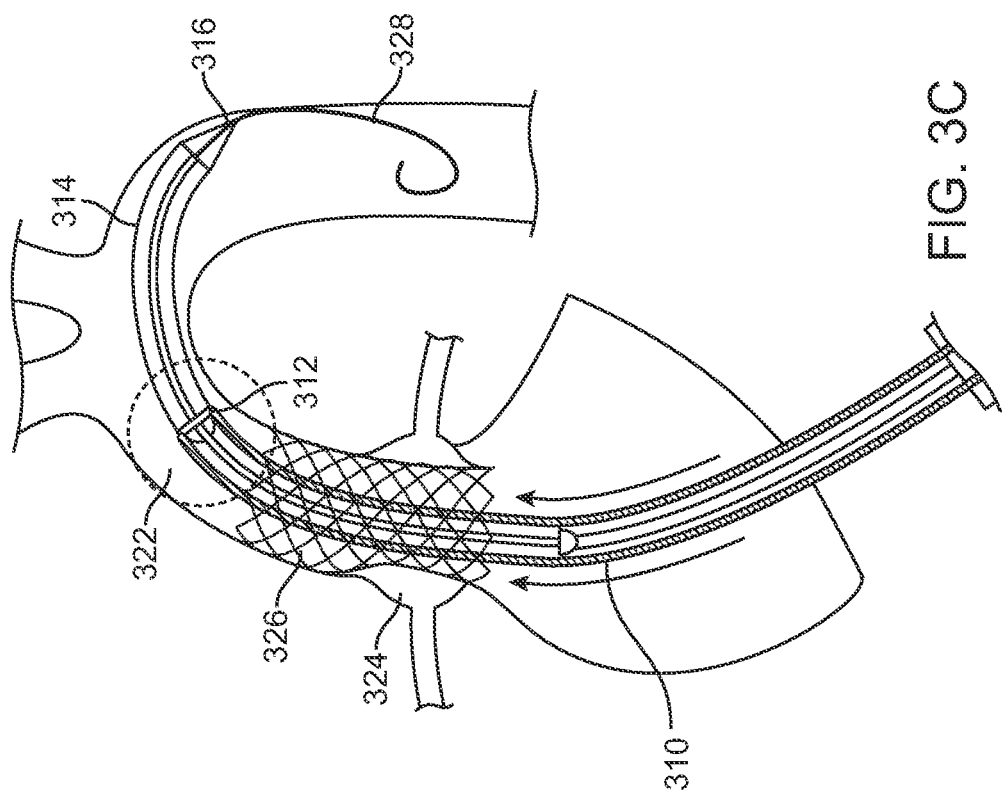
FIG. 3C illustrates the introducer being advanced to mate with the capsule after deployment of the heart valve prosthesis, according to an embodiment.

FIG. 3C illustrates introducer 310 being advanced distally through deployed heart valve prosthesis 326, as indicated by the arrows. Introducer 310 can be advanced distally, by pushing the hub in the distal direction, until introducer tip 312 contacts the proximal end of capsule 314. Medical imaging can be used to detect when introducer tip 312 contacts the proximal end of capsule 314. This can be further facilitated by embodiments where introducer tip 312 and capsule ring 318 include radiopaque materials.

FIG. 3D shows an enlarged view of introducer tip 312 mating with capsule ring 318 of capsule 314. In this embodiment, introducer tip 312 can fit over and around capsule ring 318. In certain embodiments, introducer tip 312 can have a tapered opening to facilitate mating with capsule 314. In certain embodiments, flexible distal section 310B can be expandable, providing a tight fit between introducer tip 312 and the rigid capsule ring 318 of capsule 314. In certain embodiments, the interior of introducer tip 312 and the exterior of capsule 314 can be coated with a biocompatible lubricant to further facilitate mating of the two features. Inner shaft 319 can also be retracted proximally by rotating the control knob to retract capsule 314 in the proximal direction, thereby creating an interference fit between capsule 314 and introducer tip 312 of introducer 310.

Figure 4A:
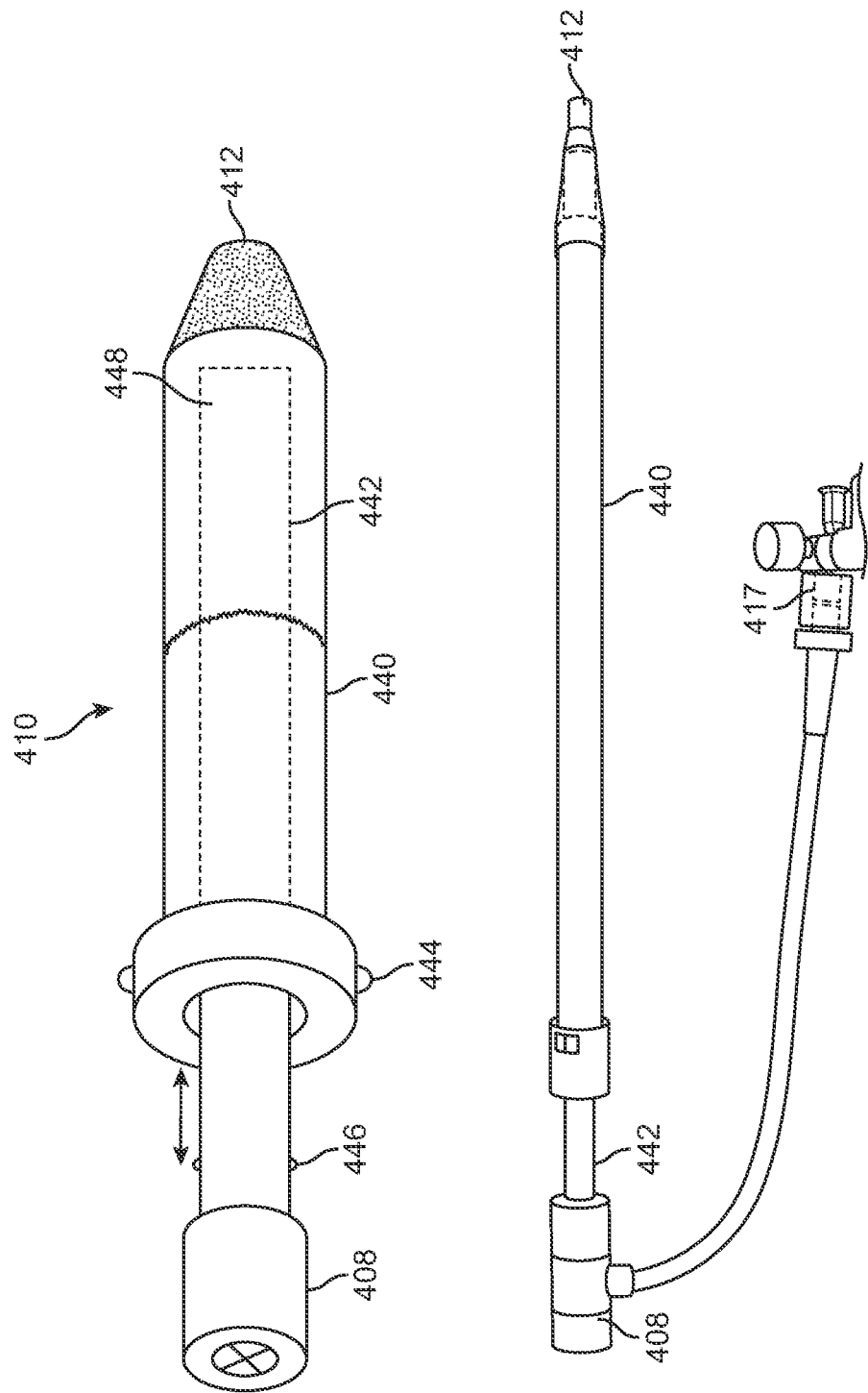

FIGS. 4A and 4B illustrate another embodiment of introducer 410. Introducer 410 can include an interior shaft 442 with flared tip 448. As shown in FIG. 4A, flared tip 448 is generally not in a flared state when inside outer shaft 440 during the prosthesis deployment stage. After introducer 410 is moved distally through the deployed prosthesis, interior shaft 442 can be advanced distally, or outer shaft 440 can be retracted proximally, so that flared tip 448 exits introducer tip 412. Introducer tip 412 can be a thin-walled, flexible tip to allow flared tip 448 to easily exit outer shaft 440. Flared tip 448 can be self-expanding so that flared tip 448 expands to a pre-formed shape after exiting introducer 410 through introducer tip 412. The capsule can then be retracted in the proximal direction to fit within flared tip 448. This can provide a smooth profile for retraction of the delivery system through the deployed prosthesis.

Introducer 410 can include locking and release mechanisms, for example, locking clips 446 and release tabs 444, capable of restricting the movement of interior shaft 442 and outer shaft 440. Once interior shaft 442 is advanced distally or outer shaft 440 is retracted proximally to a certain distance, locking clips 446 on interior shaft 442 can engage with a counterpart locking mechanism on outer shaft 440. This can restrict the movement of interior shaft 442 and outer shaft 440 relative to each other, preventing flared tip 448 from unintentionally reentering outer shaft 440 through introducer tip 412. Release tabs 444 on outer shaft 440 can be pressed to disengage locking clips 446, allowing movement of interior shaft 442 and outer shaft 440. The locking and release mechanisms can also comprise features such as pins, grooves, teeth and buttons which can prevent movement of the shafts after flared tip 448 exits introducer 410.

Figure 4C:
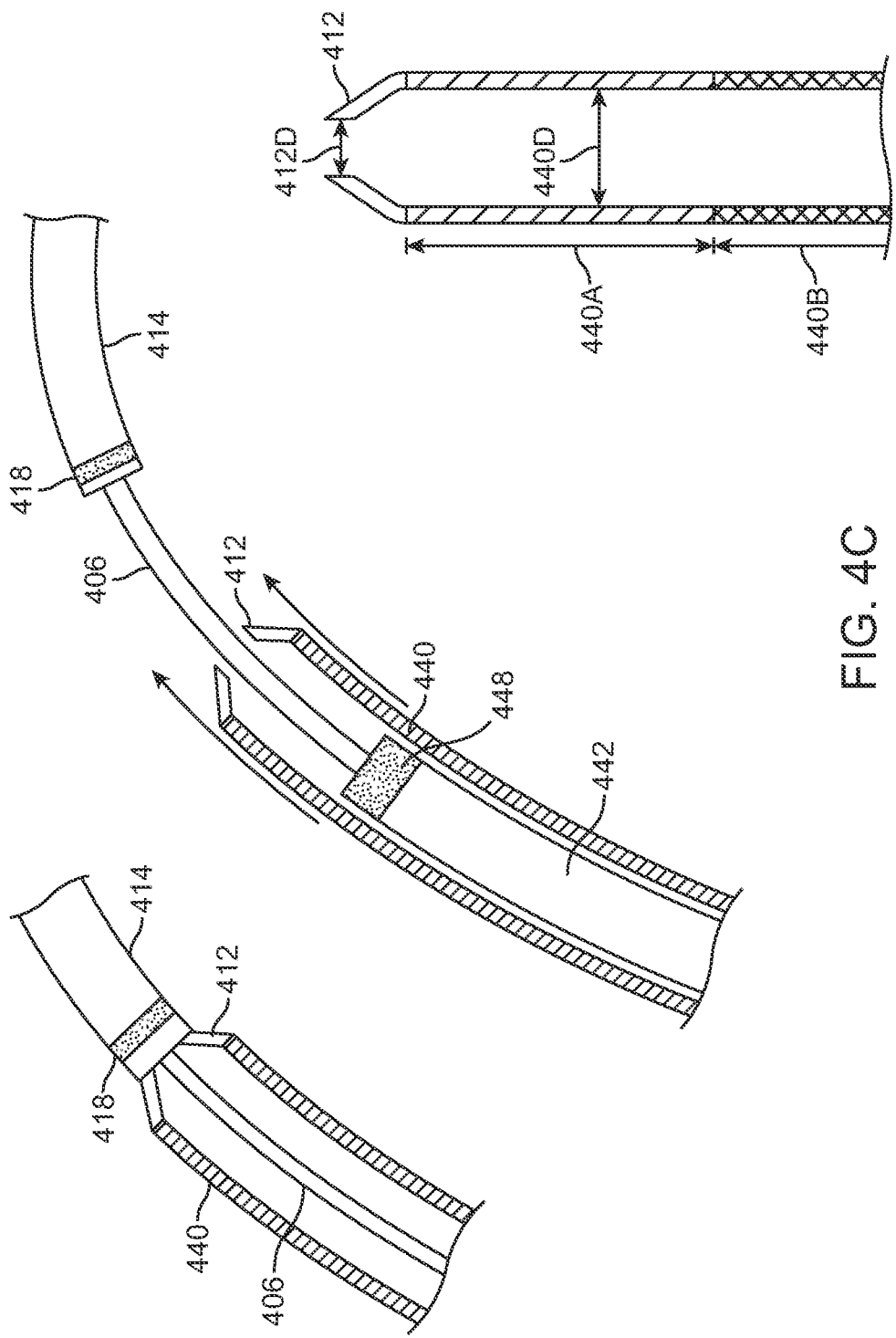
FIG. 4C illustrates deployment of the heart valve prosthesis using the introducer with the flared tip, according to an embodiment.

FIG. 4C illustrates a deployment procedure for the embodiment of FIGS. 4A-4B. FIG. 4C first shows capsule 414, and specifically capsule ring 418, mated with introducer tip 412 during the delivery stage. FIG. 4C also shows capsule 414 being advanced distally, which would deploy the prosthesis. Interior shaft 442 can then be moved distally out of introducer tip 412 of introducer 410 to expose flared tip 448. After flared tip 448 exits introducer tip 412, capsule 414 can be retracted in the proximal direction by rotating the control knob for intermediate shaft 406 to mate capsule ring 418 of capsule 414 with flared tip 448. Introducer 410 can also include hub 408 and flushing port 417, which can perform similar functions as in other embodiments.

FIG. 4C also illustrates different components of introducer 410 according to an embodiment. Outer shaft 440 can include a flexible distal portion 440A and a stiff proximal potion 440B. The diameter of outer shaft 440 is indicated by 440D. In certain embodiments, the interior of outer shaft 440 and the exterior of interior shaft 442 can be coated with a biocompatible lubricant to facilitate movement of interior shaft 442 to expose flared tip 448. Diameter 412D indicates the diameter of introducer tip 412. In certain embodiments, this diameter can expand, due to the material of introducer tip 412, as flared tip 448 exits introducer tip 412. In certain embodiments, introducer tip 412 can be biased to a tapered shape, as shown in FIGS. 4A-4C, such that if flared tip 448 is retracted into outer shaft 440, introducer tip 412 can return to its original shape and diameter.

FIGS. 5A-5C illustrate example embodiments of hub 508. Hub 508 can be used to quickly advance and retract introducer 110. FIG. 5A shows an ergonomic design of hub 508, which can allow the user to easily slide hub 508 along intermediate shaft 106, thereby advancing or retracting introducer 110. FIG. 5B shows hub 508 including a shaft grip feature, for example button clamps 550, which can include a spring-loaded button. Button clamps 550 can prevent accidental movement of hub 508, and thus introducer 110, during the procedure. Hub 508 can also include flushing port 552, which can be used for flushing introducer 110 and for maintaining hemostasis during the procedure.

FIG. 5C illustrates an interior view of hub 508 in FIG. 5B. As shown, hub 508 can include grip 556 which, in combination with button clamps 550, can create a spring-loaded mechanism for gripping intermediate shaft 106. Also shown is cavity 554 for a seal, which can prevent leakage of blood during the procedure.

FIGS. 6A and 6B illustrate spacer beads 660, according to an embodiment. Spacer beads 660 can create a step in the profile from outer shaft 640 to intermediate shaft 642. Generally, an interior surface of spacer beads 660 can contact intermediate shaft 642, and an exterior surface of spacer beads 660 can contact outer shaft 640. Spacer beads 660 can help maintain a balance of rigidity in outer shaft 640 during the delivery procedure. Spacer beads 660 can be evenly distributed along the entire length of the introducer, or located only along a portion of the introducer. For example, spacer beads 660 can be located only near the distal end of the introducer. This can provide increased rigidity at the distal end of the introducer, which can facilitate mating of introducer tip 612 with the proximal end of the capsule. Spacer beads 660 can also facilitate centering of intermediate shaft 642 within outer shaft 640, thereby further minimizing the risk of hang-ups during the retraction process. Spacer beads 660 can be made from any suitable material, such as plastic or metal. In certain embodiments, spacer beads 660 can be radiopaque so that the introducer can be detected with medical imaging during the procedure.

Figure 7:
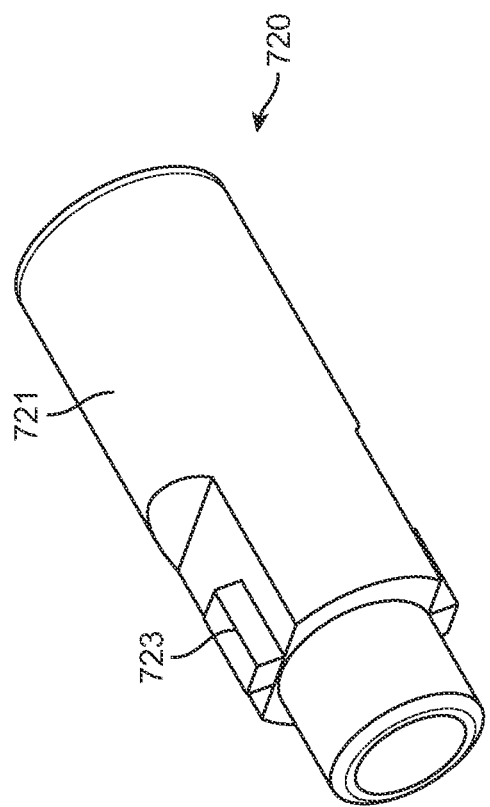
FIG. 7 illustrates a close-up view of the valve retainer, according to an embodiment.

FIG. 7 shows a close-up view of valve retainer 720, according to an embodiment. Valve retainer 720 can include clips 723 and landing zone 721. Clips 723 can be used for holding the prosthesis in place during delivery. Clips 723 can be either raised on the surface of valve retainer 720 or cut into the surface of valve retainer 720. Landing zone 721 can be a smooth surface located at the distal end of valve retainer 720. Landing zone 721 can prevent prosthesis flaring when engaged with the capsule, and can eliminate hang-up points. The proximal rigid section of the capsule, namely the capsule ring, can ride up on landing zone 721 after the capsule is advanced distally to deploy the prosthesis. An interference fit can be created between the capsule ring and landing zone 721 of valve retainer 720. This can prevent the capsule from moving too far in the distal direction during deployment of the prosthesis. The disclosed valve retainer 720 can be used with any of the previously described catheter embodiments having a valve retainer.

Figure 8:
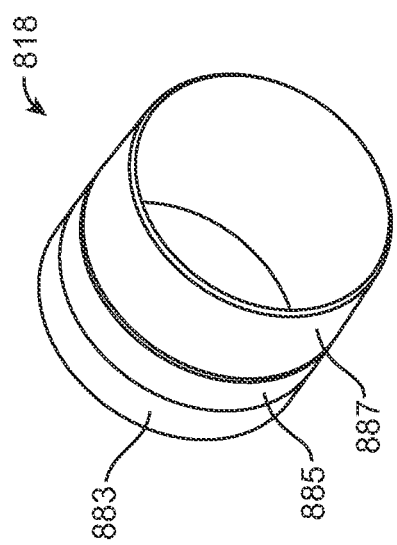
FIG. 8 illustrates a close-up view of the capsule ring, according to an embodiment.

FIG. 8 illustrates a close-up view of capsule ring 818, according to an embodiment. Capsule ring 818 can be fixed to the proximal end of the capsule. It can prevent the prosthesis from flaring and can provide a rigid collar to mate with the introducer and introducer tip, creating a continuous profile for smooth retraction of the delivery system through the deployed heart valve prosthesis. Capsule ring 818 can comprise proximal portion 883, band 885 and distal portion 887. In certain embodiments, all or part of capsule ring 818, such as band 885, can be a radiopaque material, so it can be located with medical imaging during the procedure to provide a reference point for the location of the delivery system. In certain embodiments, distal portion 887 can have a larger diameter than proximal portion 883, such that distal portion 887 fits over the landing zone of the valve retainer and proximal portion 883 creates an interference fit with the landing zone. The disclosed capsule ring 818 can be used with any of the previously described catheter embodiments having a capsule ring.

Figure 9B:
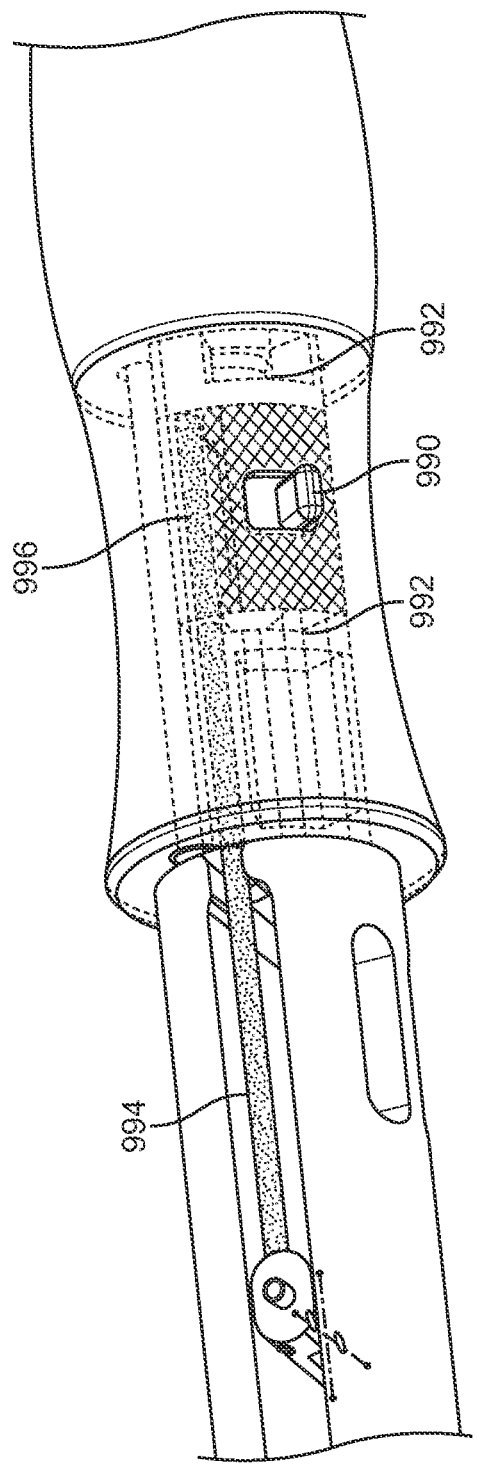
Figure 9C:
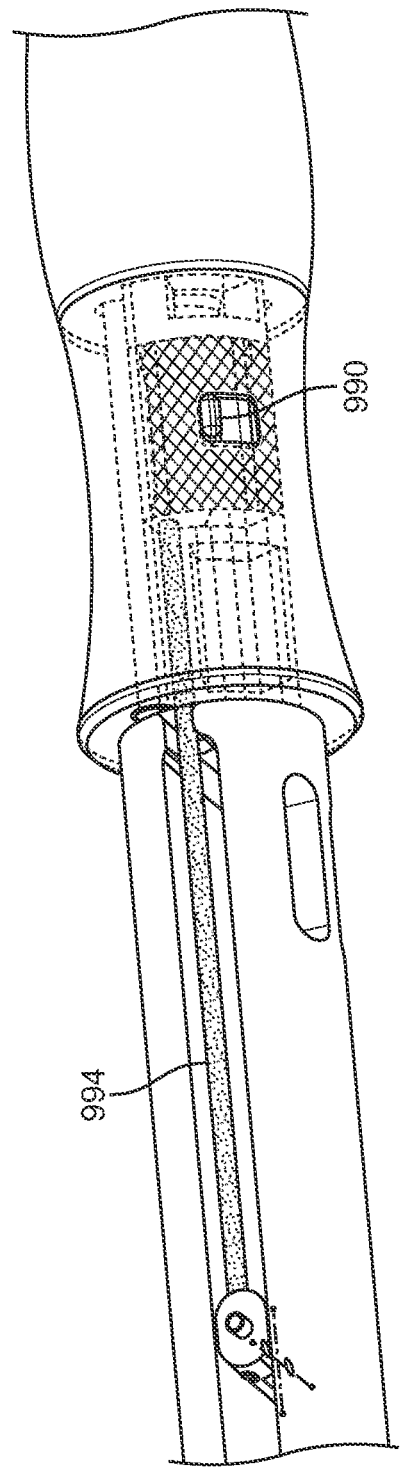

FIGS. 9A-9C illustrate a handle safety stop feature, according to an embodiment. Once the prosthesis is deployed, the system can be closed by advancing the introducer and then retracting the capsule to mate with the introducer tip. Handle 902 can include a safety stop feature that can limit the permissible retraction distance of the capsule to a preset distance. The safety stop feature can include bar 994, which can travel through slot 996 in handle 902. Once out of slot 996, spring mechanism 992 can close slot 996 where bar 994 was located, limiting the retraction distance. As shown in FIG. 9A, the safety stop feature can include latch 990 which can be accessed from an exterior of handle 902. FIGS. 9B and 9C illustrate an interior view of handle 902. As shown in FIG. 9B, bar 994 can extend into slot 996. Spring mechanism 992 can exert pressure on bar 994 such that once bar 994 exits slot 996, latch 990 can be pushed into slot 996, thus preventing bar 994 from reentering slot 996. This can limit the retraction distance of the capsule.

Methods of delivering a heart valve prosthesis are also provided. References to the Figures are made by way of example, and are not meant to be limiting. Prior to surgery, the desired valve implantation location should be determined. This can be done with the assistance of medical imaging, such as a CT scan. For prosthetic aortic valve implantation via a transapical route, the implantation location can generally be located within aortic sinus 324 such that the proximal part of heart valve prosthesis 326 engages the leaflets of the natural aortic valve, and the distal part of heart valve prosthesis 326 engages the inner wall of ascending aorta 322. Alternative implantation sites can be used, and the optimal implantation site can be determined for each individual patient.

Generally, for a transapical procedure, the chest can be prepared in the normal manner and the heart can be accessed at the apex. This can be accomplished, for example, by a mini-sternotomy or a thoracotomy. In certain instances, an incision can be made at the apex of the heart and a hemostatic valve can be secured to the heart to provide an entry point for the delivery system. The user can place the delivery system, which can include a pre-loaded, radially collapsed heart valve prosthesis 326 within capsule 114, over a guide wire and advance the system through the incision at the apex of the heart.

The user can advance the system until capsule ring 218 is lined up, for example, with the basal plane of the aortic valve. In certain embodiments, medical imaging can be used to locate features of the delivery system, such as capsule tip 116 or capsule ring 218, to facilitate positioning the delivery system at the desired deployment location.

Once in the desired anatomical position, capsule 114 can be advanced distally to deploy the prosthesis. Generally, heart valve prosthesis 326 can be a self-expanding prosthetic valve, such that it will expand to a pre-fabricated size and shape within aortic sinus 324 after being deployed. The user can then advance introducer 110 distally by pushing hub 108 in the distal direction. Introducer 110 can be advanced until introducer tip 112 contacts valve retainer 220. Capsule 114 can then be retracted proximally to mate with introducer tip 112. This can provide a continuous profile for the delivery system during retraction through the deployed prosthesis. The user can then withdraw the delivery system from the body and complete the procedure as normal, such as by suturing the insertion point at the apex of the heart.

The foregoing description has been presented for purposes of illustration and description. It is not intended to be exhaustive or to limit the precise embodiments disclosed. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. A prosthesis delivery system comprising:
a handle assembly including a rotatable control knob;
an intermediate shaft extending from the handle assembly and having an interior lumen, the intermediate shaft having a prosthesis retaining element connected to a distal end thereof;
an introducer shaft having an interior lumen and a tapered introducer tip attached at a distal end thereof, wherein a proximal end of the introducer shaft is connected to a hub secured to the intermediate shaft and configured to slide in a proximal and distal direction along the intermediate shaft;
an inner shaft extending from the handle assembly and configured to be moved in a proximal direction by rotating the control knob in a first direction and to be advanced in a distal direction by rotating the control knob in a second direction that is opposite of the first direction; and
a capsule including a proximal end, a distal end and a capsule tip, wherein the distal end of the capsule is connected to a distal end of the inner shaft, the proximal end of the capsule is configured to have an interference fit with the prosthesis retaining element of the intermediate shaft in a deployment stage and to receive the tapered introducer tip in each of a delivery stage and a retraction stage, and the capsule is configured to contain a prosthesis device, and
wherein when the control knob is rotated in the second direction the inner shaft and the capsule advance together in the distal direction relative to the prosthesis device until the proximal end of the capsule contacts the prosthesis retaining element and thereafter further distal advancement is prevented.

2. The prosthesis delivery system of claim 1, wherein the prosthesis retaining element has an interior lumen.

3. The prosthesis delivery system of claim 2, wherein the prosthesis retaining element comprises a distal cylindrical surface and at least one protrusion or indentation located at a proximal end of the retaining element and configured to correspond to a retaining element on a prosthesis device.

4. The prosthesis delivery system of claim 1, wherein the capsule further comprises a stiffening ring located at the proximal end of the capsule.

5. The prosthesis delivery system of claim 1, further comprising a plurality of spacer beads having an interior surface and an exterior surface, wherein the interior surface of the spacer beads contact an exterior surface of the intermediate shaft, and wherein the exterior surface of the spacer beads contact an interior surface of the introducer shaft.

6. The prosthesis delivery system of claim 1, further comprising an interior shaft including a flared distal tip.

7. The prosthesis delivery system of claim 6, further comprising a locking mechanism configured to prevent movement of the introducer shaft in relation to the second intermediate shaft when in a locked position.

8. The prosthesis delivery system of claim 7, further comprising a release mechanism located on an exterior of the introducer shaft, wherein pressing the release mechanism releases the introducer shaft from the locked position.

9. The prosthesis delivery system of claim 1, wherein the hub further comprises at least one release tab, wherein pressing the release tab allows the hub to slide in the proximal and distal directions along the intermediate shaft.

10. The prosthesis delivery system of claim 1, wherein the handle further comprises a safety latch configured to limit a distance the inner shaft can be retracted in the proximal direction.

11. A method of implanting a prosthesis in a body lumen using a catheter, the catheter comprising:
a handle assembly including a rotatable control knob;
an intermediate shaft extending from the handle assembly and having an interior lumen;
an introducer shaft having an interior lumen and an introducer tip, wherein the introducer shaft is connected to a hub secured to the intermediate shaft and configured to slide in a proximal and distal direction along the intermediate shaft;
an inner shaft extending from the handle assembly and configured to be moved in a proximal direction by rotating the control knob in a first direction and to be advanced in a distal direction by rotating the control knob in a second direction that is opposite of the first direction; and
a capsule including a proximal end, a distal end and a capsule tip, wherein the distal end of the capsule is connected to a distal end of the inner shaft, and wherein the capsule is configured to contain a prosthesis device;
the method comprising:
inserting the catheter into a body lumen;
advancing the catheter to a deployment location;
advancing the capsule distally to deploy the prosthesis device, wherein rotating the control knob on the handle assembly in the second direction advances the inner shaft and capsule distally;
advancing the introducer shaft through the deployed prosthesis device until the introducer tip engages the proximal end of the capsule;
retracting the catheter proximally through the deployed prosthesis device; and
removing the catheter from the body lumen.

12. The method of claim 11, further comprising:
retracting the capsule proximally after advancing the introducer shaft through the deployed prosthesis device to mate the proximal end of the capsule with the introducer tip.

13. The method of claim 11, wherein rotating the control knob on the handle assembly in the first direction retracts the inner shaft and the capsule proximally.

14. The method of claim 11, wherein advancing the introducer shaft through the deployed prosthesis device comprises sliding the hub distally along the intermediate shaft.

15. The method of claim 11, wherein the catheter is inserted through an apex of a heart.

16. The method of claim 15, wherein the catheter is advanced until a stiffening ring located at the proximal end of the capsule is lined up with a basal plane of an aortic valve.

17. The method of claim 11, further comprising proximally retracting the introducer shaft to expose a flared tip of a second intermediate shaft after advancing the introducer shaft through the deployed prosthesis device.

18. The method of claim 17, wherein the introducer shaft engages at least one locking clip located on the second intermediate shaft after being retracted to prevent distal or proximal movement of the introducer shaft.

19. The method of claim 11, wherein the capsule is advanced distally until a stiffening ring located at the proximal end of the capsule engages a prosthesis retaining element connected to a distal end of the intermediate shaft.

20. The method of claim 11, wherein the prosthesis device is a self-expandable heart valve prosthesis.

\* \* \* \* \*